(12) United States Patent
Li et al.

(10) Patent No.: US 10,390,886 B2
(45) Date of Patent: Aug. 27, 2019

(54) IMAGE-BASED PEDICLE SCREW POSITIONING

(71) Applicant: Siemens Medical Solutions USA, Inc., Malvern, PA (US)

(72) Inventors: Mingzhong Li, Rolla, MO (US); Shu Liao, Chester Springs, PA (US); Fitsum Aklilu Reda, West Chester, PA (US); Yiqiang Zhan, Berwyn, PA (US); Xiang Sean Zhou, Exton, PA (US); Gerhard Kleinszig, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 41 days.

(21) Appl. No.: 15/281,182

(22) Filed: Sep. 30, 2016

(65) Prior Publication Data

US 2017/0112575 A1   Apr. 27, 2017

Related U.S. Application Data

(60) Provisional application No. 62/246,201, filed on Oct. 26, 2015.

(51) Int. Cl.
  *A61B 3/10* (2006.01)
  *A61B 34/10* (2016.01)
  *G06T 7/73* (2017.01)

(52) U.S. Cl.
  CPC ............... *A61B 34/10* (2016.02); *G06T 7/73* (2017.01); *A61B 2034/105* (2016.02);
  (Continued)

(58) Field of Classification Search
  CPC ........ A61B 2034/105; A61B 2034/107; A61B 2034/102; A61B 2034/2051; A61B 2034/2072; A61B 2034/252; A61B 2034/254; A61B 2034/256; A61B 2090/365; A61B 34/20; A61B 34/25; A61B 34/10; A61B 17/00234; A61B 17/1671; A61B 5/407; A61B 17/1626; A61B 17/1703; A61B 17/032; A61B 2017/00022; A61B 2017/00221; A61B 2090/061; A61B 2562/0247; A61B 2562/043; A61B 2034/2055; A61B 10/0275; A61B 2090/3966; A61B 2090/374; A61B 2010/0208; A61B 2034/301; A61B 2090/378; A61B 2090/39; A61B 17/1615; A61B 2090/3975; G06T 7/0012;
  (Continued)

(56) References Cited

U.S. PATENT DOCUMENTS

| 8,160,676 B2 * | 4/2012 | Gielen .................... A61B 5/06 |
| | | 382/128 |
| 2004/0152972 A1 * | 8/2004 | Hunter ................. A61B 17/025 |
| | | 600/424 |

(Continued)

*Primary Examiner* — Aklilu K Woldemariam

(57) ABSTRACT

A framework for pedicle screw positioning is described herein. In accordance with one aspect, the framework segments at least one vertebra of interest in image data. The framework then automatically determines a pedicle region within the segmented vertebra of interest, and a safe region within the segmented vertebra of interest. An optimal insertion path passing through the pedicle region may then be generated within the safe region.

20 Claims, 8 Drawing Sheets

(52) U.S. Cl.
CPC .............. *A61B 2034/107* (2016.02); *G06T 2207/10081* (2013.01); *G06T 2207/10088* (2013.01); *G06T 2207/20081* (2013.01); *G06T 2207/30012* (2013.01); *G06T 2207/30052* (2013.01)

(58) Field of Classification Search
CPC . G06T 2207/30008; G06T 7/337; G06T 7/35; G06T 2207/20104; G06T 2207/20212; G06T 3/0068; G06T 7/60; G06T 2210/41; G06T 19/20; G06T 2207/30052; G06T 7/20; G06T 11/006; G06T 11/00; G06T 2207/30016; G06T 2207/10088; G06T 7/32; G06T 7/73; G06T 2207/10072; A61F 2002/4666; A61F 2/4455; A61F 2/4611; A61F 2/4657; A61F 2310/00023; A61F 2002/2835; A61F 2002/30011; A61F 2002/3085; A61F 2002/4475; A61F 2/4684; A61F 2/442; A61F 2002/30607
USPC ........ 382/128, 129, 130, 131, 132; 600/418, 600/426
See application file for complete search history.

(56) References Cited

U.S. PATENT DOCUMENTS

| | | | | |
|---|---|---|---|---|
| 2004/0171924 A1* | 9/2004 | Mire | ............... | A61B 34/20 600/407 |
| 2005/0075644 A1* | 4/2005 | DiPoto | ............... | A61B 1/3135 606/90 |
| 2005/0085714 A1* | 4/2005 | Foley | ............... | A61B 17/1735 600/424 |
| 2006/0085068 A1* | 4/2006 | Barry | ............... | A61B 17/1615 623/17.11 |
| 2006/0098897 A1* | 5/2006 | Dewaele | ............... | G06K 9/6203 382/294 |
| 2006/0224078 A1* | 10/2006 | Hoey | ............... | A61B 5/0537 600/546 |
| 2007/0016296 A1* | 1/2007 | Triplett | ............... | A61B 17/1671 623/17.11 |
| 2007/0239159 A1* | 10/2007 | Altarac | ............... | A61B 17/025 606/86 A |
| 2007/0242869 A1* | 10/2007 | Luo | ............... | G06K 9/00 382/132 |
| 2009/0082666 A1* | 3/2009 | Geist | ............... | A61B 17/7083 600/424 |
| 2010/0234725 A1* | 9/2010 | Geist | ............... | A61B 17/7002 600/424 |
| 2010/0331883 A1* | 12/2010 | Schmitz | ............... | A61B 10/0275 606/249 |
| 2012/0022357 A1* | 1/2012 | Chang | ............... | A61B 6/022 600/407 |
| 2012/0022597 A1* | 1/2012 | Gephart | ............... | A61B 17/3421 606/279 |
| 2012/0143090 A1* | 6/2012 | Hay | ............... | A61B 6/505 600/587 |
| 2012/0179214 A1* | 7/2012 | Geist | ............... | A61B 17/7002 606/86 A |
| 2013/0076157 A1* | 3/2013 | Stein | ............... | A61F 2/442 307/116 |
| 2013/0079678 A1* | 3/2013 | Stein | ............... | A61B 5/103 600/594 |
| 2017/0135706 A1* | 5/2017 | Frey | ............... | A61B 17/1703 |

* cited by examiner

IMAGE-BASED PEDICLE SCREW POSITIONING

CROSS-REFERENCE TO RELATED APPLICATION

The present application claims the benefit of U.S. provisional application No. 62/246,201 filed Oct. 26, 2015, the entire contents of which are herein incorporated by reference.

TECHNICAL FIELD

The present disclosure generally relates to digital medical data processing, and more particularly to a image-based pedicle screw positioning.

BACKGROUND

The field of medical imaging has seen significant advances since the time X-Rays were first used to determine anatomic abnormalities. Medical imaging hardware has progressed in the form of newer machines such as Magnetic Resonance Imaging (MRI) scanners, Computed Axial Tomography (CAT) scanners, etc. Because of the large amount of image data generated by such modern medical scanners, there has been and remains a need for developing image processing techniques that can automate some or all of the processes to determine the presence of anatomic abnormalities in scanned medical images.

Digital medical images are constructed using raw image data obtained from a scanner, for example, a CAT scanner, MRI, etc. Digital medical images are typically either a two-dimensional ("2D") image made of pixel elements or a three-dimensional ("3D") image made of volume elements ("voxels"). Such 2D or 3D images are processed using medical image recognition techniques to determine the presence of anatomic structures such as cysts, tumors, polyps, etc. Given the amount of image data generated by any given image scan, it is preferable that an automatic technique should point out anatomic features in the selected regions of an image to a doctor for further diagnosis and planning treatment of a disease or medical condition.

Spine stabilization is one of the most common treatment methods for various spinal diseases, such as scoliosis and spondylolisthesis. Pedicle screw fixation plays an important role in spine stabilization surgery. A pedicle is a small bony protuberance that projects from the back of each vertebra and connects the lamina to the vertebral body to form the vertebral arch. There are two pedicles per vertebra, one branching to the left and one branching to the right. Screws inserted into the pedicles provide a means to grip a spinal segment to rigidly stabilize both ventral and dorsal aspects of the spine. Pedicle screws serve as firm anchor points that can be connected with a rod. The screws may be placed at two or three consecutive spine segments and connected with a short rod to prevent motion at the segments that are being fused.

Due to close proximity of the pedicles to the spinal canal and surrounding vessels, misplaced pedicle screws can lead to serious complications. Treatment plans should ensure safe placement of the pedicle screws. Specific treatment plans are typically manually determined by radiologists or physicians. Such manual determination is very time consuming, and may not be reproducible cross-operations.

SUMMARY

Described herein is a framework for pedicle screw positioning. In accordance with one aspect, the framework segments at least one vertebra of interest in image data. The framework then automatically determines a pedicle region within the segmented vertebra of interest, and a safe region within the segmented vertebra of interest. An optimal insertion path passing through the pedicle region may then be generated within the safe region.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
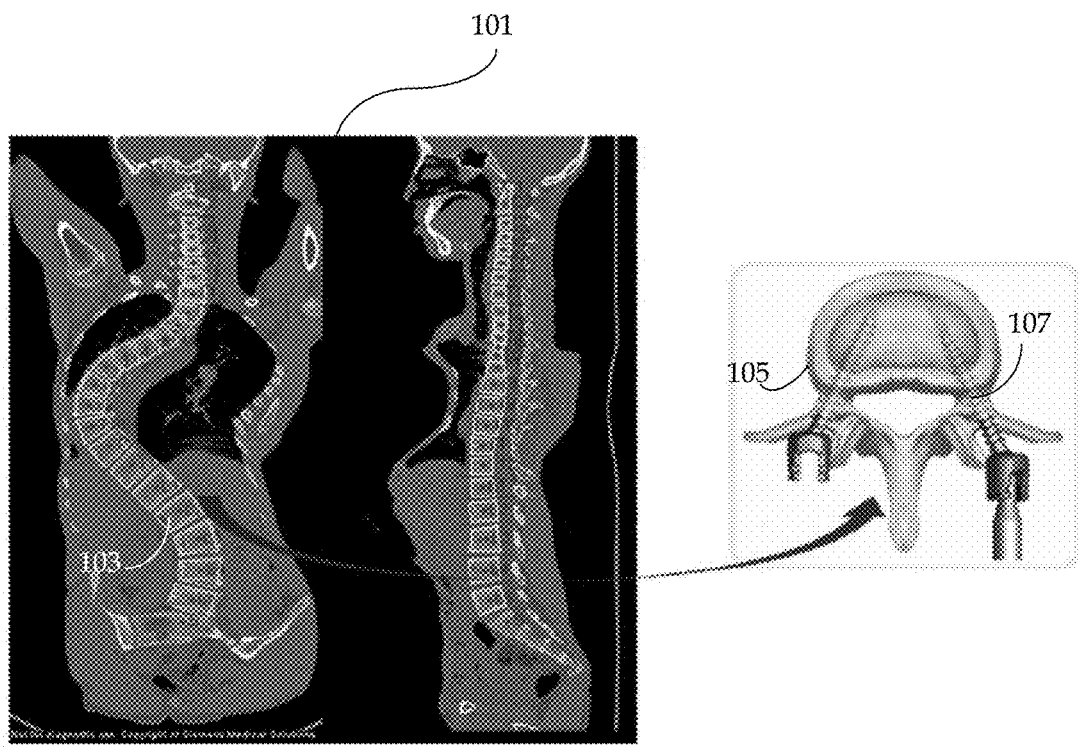
FIG. 1 illustrates an exemplary pedicle screw insertion for spine stabilization of a scoliosis patient.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

Pedicle screw fixation plays an important role in spine stabilization surgery. FIG. 1 illustrates an exemplary pedicle screw insertion for spine stabilization of a scoliosis patient. In the surgery planning stage, a computed tomography (CT) scan image 101 of the spine 103 may be preoperatively acquired from the patient. During the surgery, a burr may first be used to open the superficial cortex of the entry point. A pedicle probe may then be used to navigate down the isthmus of the pedicle into the vertebral body 105 along an appropriate insertion path or trajectory. A pedicle screw 107 with an appropriate diameter and length is then carefully inserted along the same path created.

Current techniques typically require multiple screenings and measurements for each vertebra to derive the appropriate pedicle screw insertion path during surgery planning. First, each vertebra in the CT image 101 is manually reoriented to make the normal direction of the vertebral body perpendicular to the axial direction. Then, the pedicle location and the pedicle neck width are manually measured. Finally, the pedicle screw insertion path is manually determined. These steps are time-consuming and may not be reproducible cross-operations. Moreover, other factors such as patient's age and bone density, should also be considered during the planning stage. For instance, more conservative pedicle screw insertion schemes are needed for elder patients with relatively low bone density.

A framework for automatically positioning pedicle screws is described herein. In accordance with one aspect, the framework automatically labels each vertebra in the spine portion (e.g., using spine landmark detection) and segments each vertebra (e.g., using multi-atlas vertebrae segmentation). The framework subsequently determines pedicle regions within the segmented vertebrae and safe regions within the vertebrae for pedicle screw insertion. An optimal insertion path that passes through a pedicle region may then be determined within one of the safe regions.

The framework may enable human interaction to adaptively suggest possible pedicle screw insertion paths based on one or more clinical parameters, such as patient age, desired conservativeness level, pedicle screw size, etc. The framework advantageously improves the efficiency of clinical workflows and productivity of radiologists and surgeons in performing spine surgery. These and other exemplary advantages and features will be described in more detail herein.

Figure 2:
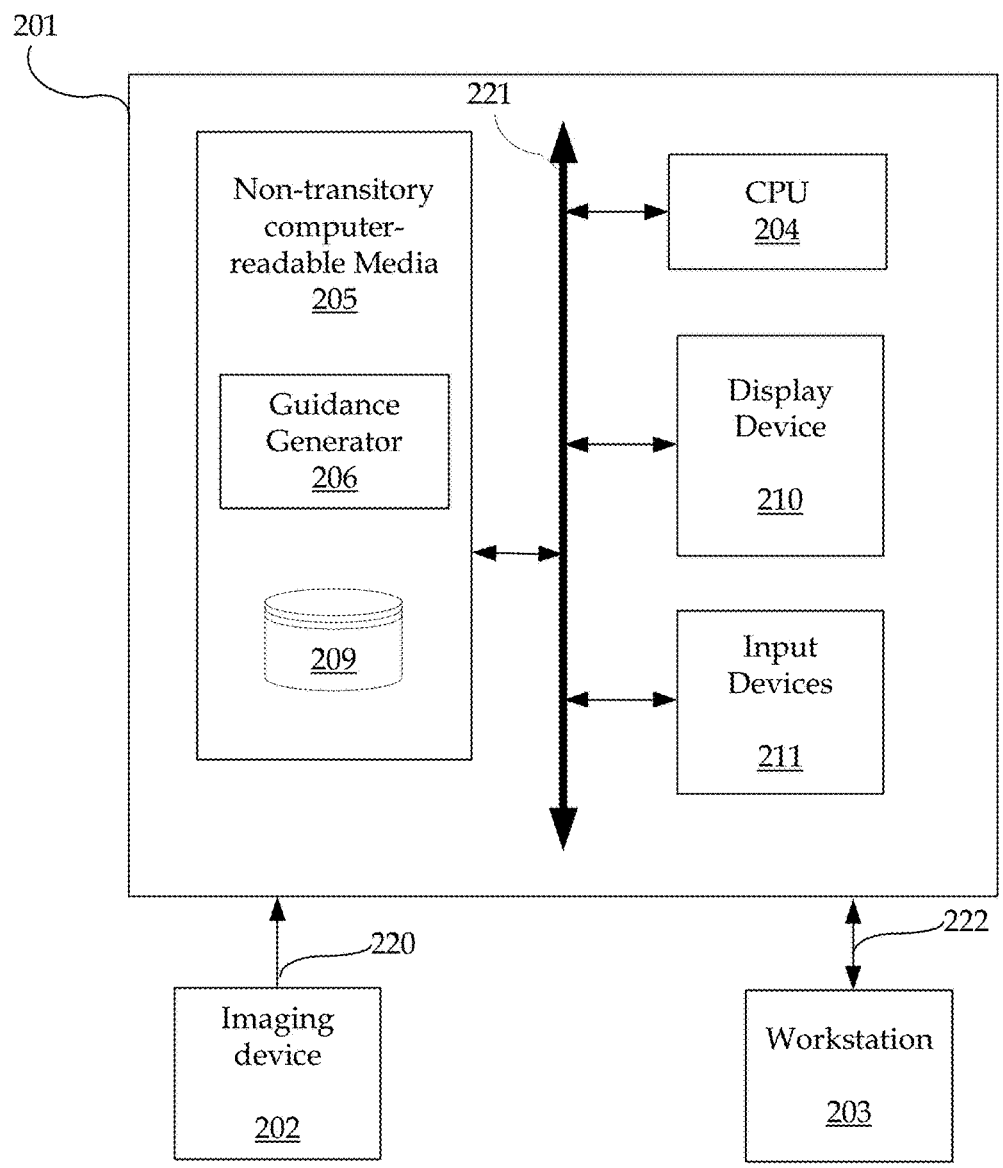
FIG. 2 is a block diagram illustrating an exemplary system.

FIG. 2 is a block diagram illustrating an exemplary system 200. The system 200 includes a computer system 201 for implementing the framework as described herein. In some implementations, computer system 201 operates as a standalone device. In other implementations, computer system 201 may be connected (e.g., using a network) to other machines, such as imaging device 202 and workstation 203. In a networked deployment, computer system 201 may operate in the capacity of a server (e.g., thin-client server, such as Syngo.Via® by Siemens Healthcare), a cloud computing platform, a client user machine in server-client user network environment, or as a peer machine in a peer-to-peer (or distributed) network environment.

In some implementations, computer system 201 comprises a processor or central processing unit (CPU) 204 coupled to one or more non-transitory computer-readable media 205 (e.g., computer storage or memory), display device 210 (e.g., monitor) and various input devices 211 (e.g., mouse or keyboard) via an input-output interface 221. Computer system 201 may further include support circuits such as a cache, a power supply, clock circuits and a communications bus. Various other peripheral devices, such as additional data storage devices and printing devices, may also be connected to the computer system 201.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 205. In particular, the present techniques may be implemented by a guidance generator 206 and a database 209.

Non-transitory computer-readable media 205 may include random access memory (RAM), read-only memory (ROM), magnetic floppy disk, flash memory, and other types of memories, or a combination thereof. The computer-readable program code is executed by CPU 204 to process medical data retrieved from, for example, imaging device 202. As such, the computer system 201 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 205 may be used for storing a database (or dataset) 209. Such data may also be stored in external storage or other memories. The external storage may be implemented using a database management system (DBMS) managed by the CPU 204 and residing on a memory, such as a hard disk, RAM, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Imaging device 202 acquires medical image data 220 associated with at least one patient. Such medical image data 220 may be processed and stored in database 209. Imaging device 202 may be a radiology scanner (e.g., X-ray, MR or a CT scanner) and/or appropriate peripherals (e.g., keyboard and display device) for acquiring, collecting and/or storing such medical image data 220.

The workstation 203 may include a computer and appropriate peripherals, such as a keyboard and display device, and can be operated in conjunction with the entire system 200. For example, the workstation 203 may communicate directly or indirectly with the imaging device 202 so that the medical image data acquired by the imaging device 202 can be rendered at the workstation 203 and viewed on a display device. The workstation 203 may also provide other types of medical data 222 of a given patient. The workstation 203 may include a graphical user interface to receive user input via an input device (e.g., keyboard, mouse, touch screen voice or video recognition interface, etc.) to input medical data 222.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 3A:
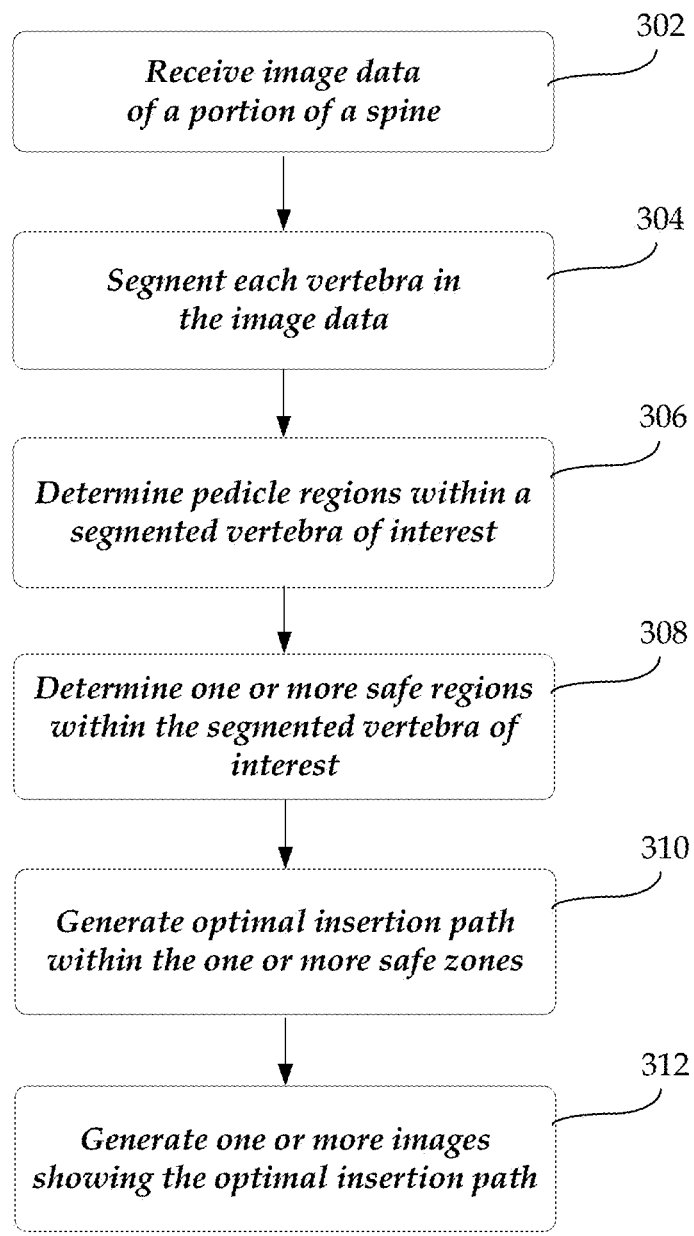
FIG. 3a shows an exemplary method of pedicle screw positioning.

FIG. 3a shows an exemplary method 300 of pedicle screw positioning by a computer system. It should be understood that the steps of the method 300 may be performed in the order shown or a different order. Additional, different, or fewer steps may also be provided. Further, the method 300 may be implemented with the system 201 of FIG. 2, a different system, or a combination thereof.

At 302, guidance generator 206 receives image data of at least a portion of a spine (or vertebral column) of a given patient under study. The image data may be acquired from the patient by, for example, imaging device 202 using techniques such as magnetic resonance (MR) imaging, computed tomography (CT), helical CT, X-ray, angiography, positron emission tomography (PET), fluoroscopy, ultrasound, single photon emission computed tomography (SPECT), or a combination thereof. The image data may be two-dimensional or three-dimensional.

At 304, guidance generator 206 segments each vertebra of the spine in the image data. In accordance with some implementations, guidance generator 206 performs automatic spine labeling and vertebra segmentation. To perform the segmentation, a set of key landmarks may be pre-defined to characterize the semantic and topological information of the spine and each vertebra. The landmarks may be pre-defined at key locations (e.g., center of each vertebra). A machine learning-based engine may be trained offline using a set of training images annotated with these pre-defined landmarks. The trained engine may then be used to detect such landmarks in the image data. Based on the detected landmarks, a region of interest (ROI) may be extracted containing each vertebra. Each vertebra within the ROI may then be segmented without confusion caused by its neighboring vertebrae. The segmentation process may automatically generate semantic labels that identify the segmented vertebrae, such as cervical, thoracic and/or lumbar vertebra labels. Based on the segmentation results, a vertebral distance map (e.g., 3D map) may be generated. The value at each voxel (or pixel) on the vertebral distance map represents the distance the voxel (or pixel) is to the nearest vertebral edge. The smaller the value, the closer the voxel (or pixel) is to the vertebral edge.

Alternatively, or additionally, a multi-atlas segmentation scheme may also be performed. The vertebrae in the training images may be manually segmented to build a set of vertebral atlases for training a landmark detection engine offline. For image data acquired from the given patient under study, the corresponding landmarks in the image data are detected using the trained landmark detection engine. A region of interest (ROI) containing each vertebra may be extracted based on the detected landmarks. Each vertebral atlas is registered to the target vertebra within the ROI using a transformation model. The transformation model may be based on rigid, affine, or deformable transformations. After registration, intelligent fusion methods may be applied to derive the final segmentation results on the target vertebra based on the registered atlases. The fusion method may be, for example, a majority voting technique or a non-local mean-based label fusion technique.

Figure 3B:
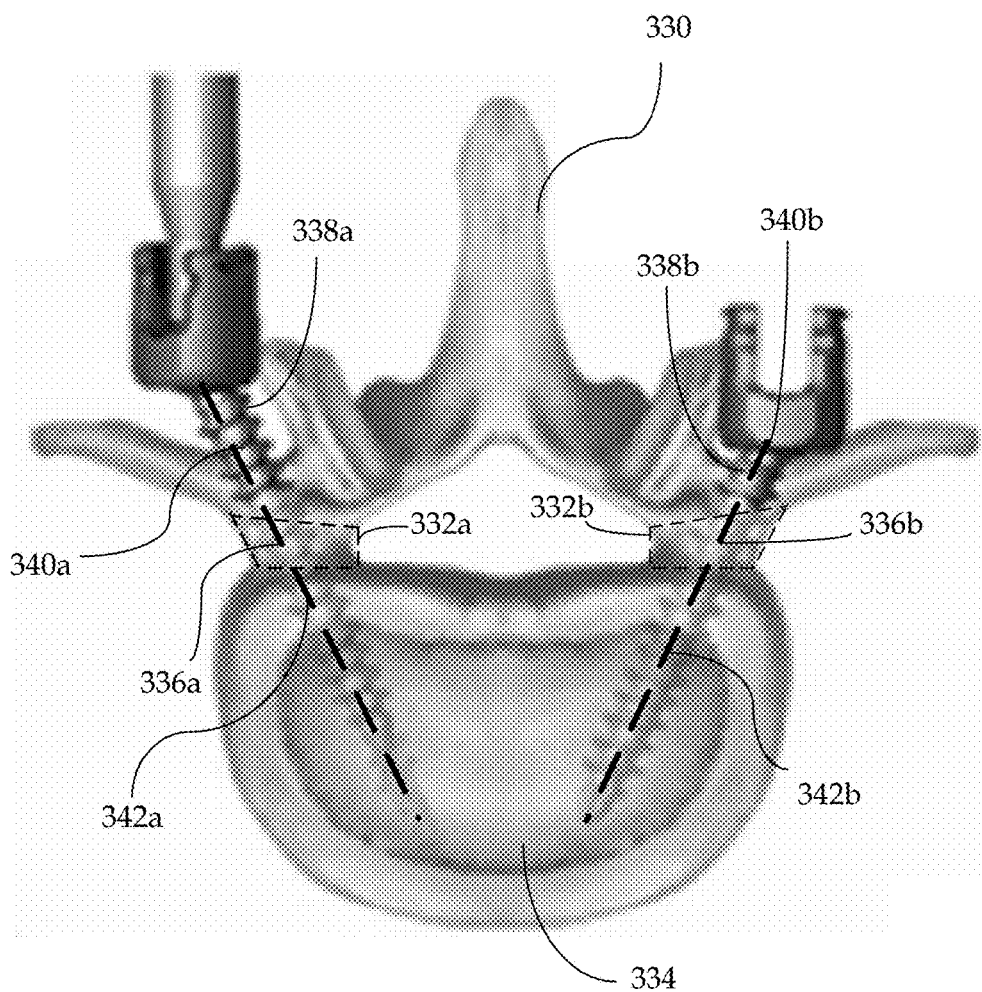
FIG. 3b shows an exemplary vertebra.

At 306, guidance generator 206 determines pedicle regions within a segmented vertebra of interest. One or more vertebrae of interest may be identified by, for example, user input received at workstation 203 for performing spine stabilization. FIG. 3b shows an exemplary vertebra of interest 330. Two pedicle regions 332a-b may be detected for each segmented vertebra of interest 330. In some implementations, clustering and morphological operations are performed on the vertebral distance map to determine the two pedicle regions 332a-b. Exemplary clustering algorithms include, but are not limited to, K-means or agglomerative clustering. Morphological erosion may be performed to obtain the three largest isolated cluster centers, which normally correspond to the vertebral body and two pedicle regions. The pedicle regions 332a-b may then be identified as the two "thin" parts protruding from the vertebral body 334.

The center 336a-b and radius of pedicle necks may be automatically, manually or semi-automatically calibrated in the image data. A pedicle distance map (e.g., 3D map) may also be generated as a result. The value at each voxel (or pixel) on the pedicle distance map represents the distance of the voxel (or pixel) to the nearest pedicle bone edges. The smaller the value, the closer the voxel (or pixel) is to the pedicle bone edges.

Returning to FIG. 3a, at 308, guidance generator 206 determines one or more safe regions within the segmented vertebra of interest. A safe region is a zone within a vertebra where the pedicle screw may be safely inserted without invading other anatomical structures (e.g., nerves). Part of the safe region includes a sub-area of the pedicle region where the pedicle screw may be safely inserted without touching or breaking through a wall of the pedicle or other anatomical structures. The safe region should be wider than the width of the pedicle screw, particularly within the pedicle region to avoid the pedicle screw breaking through the wall of the pedicle or other anatomical structures.

Safe regions may be determined by, for example, a thresholding algorithm. In some implementations, each voxel (or pixel) within the segmented vertebra is processed to determine a distance of the voxel (or pixel) from the nearest vertebral edge. Such "distance" information may be directly obtained from the vertebral distance map if already available. Voxels (or pixels) that are associated with distances greater than a threshold distance are assigned to the safe region.

The threshold distance may be associated with a conservative value. Lower conservative values are associated with smaller threshold distances. For instance, for a less conservative level, a threshold distance of 5 may be used to generate safe regions which have voxels with distances that are greater than 5 voxels to their closest bone edges. For a more conservative level, threshold distance of 10 may be used, which means only voxels that have greater than 10 voxel distances to their closest vertebral bone edges are considered part of the safe region. Accordingly, different safe regions may be generated by applying different threshold distances according to different conservative levels as desired.

In some implementations, the safe regions are adaptively calculated with respect to various clinical parameters, such as the patient's age, pedicle screw size, bone density and/or desired conservative level. A higher conservative level may be desired in cases where, for example, the patient is older or has a lower bone density. A user interface displayed at workstation 203 may be configured to enable a user to input such clinical parameters. Alternatively, some or all of these clinical parameters (e.g., pedicle screw diameter and length) are automatically derived based on the safe region and displayed as recommendations for a treatment plan.

Referring to FIG. 3b, maximum diameters of the pedicle screws 338a-b may be automatically derived by measuring the width of the safe regions within the pedicle regions 332a-b. As another example, minimum lengths of pedicle screws 338a-b may be automatically derived by measuring the depth of the safe regions within the vertebra 330 from the desired entry points 340a-b to the vertebral body 334.

Figure 4:
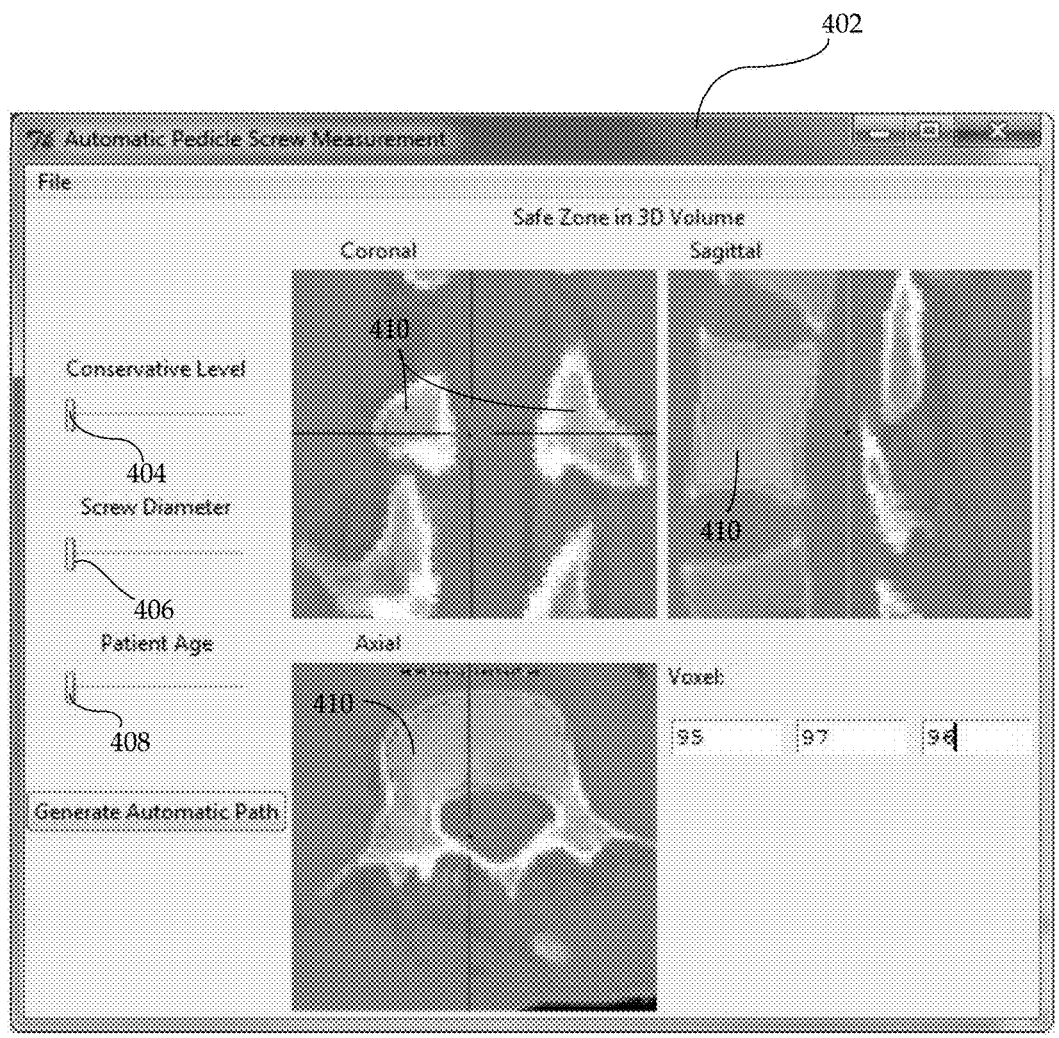
FIG. 4 shows an exemplary user interface screen indicating safe regions highlighted with respect to a low conservative level.
Figure 5:
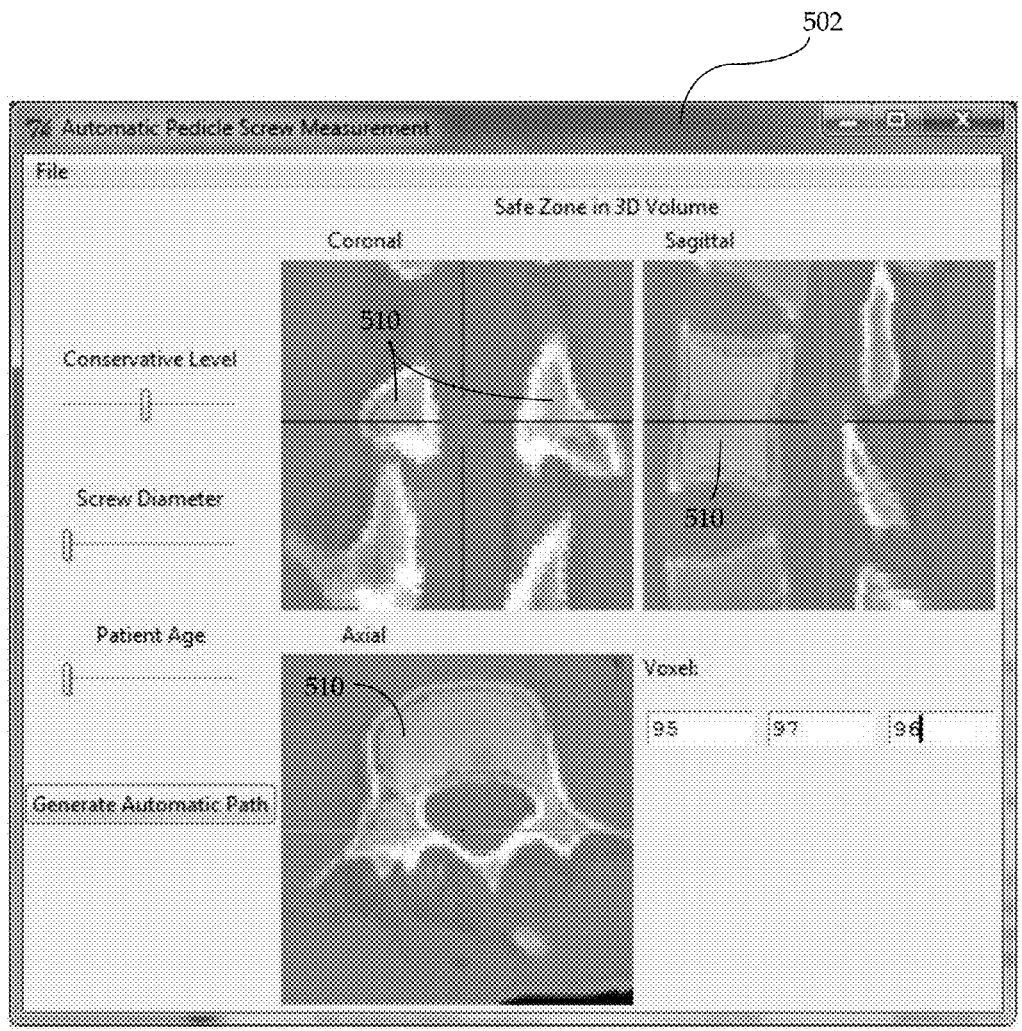
FIG. 5 shows an exemplary user interface screen indicating safe regions highlighted with respect to a mid-conservative level.
Figure 6:
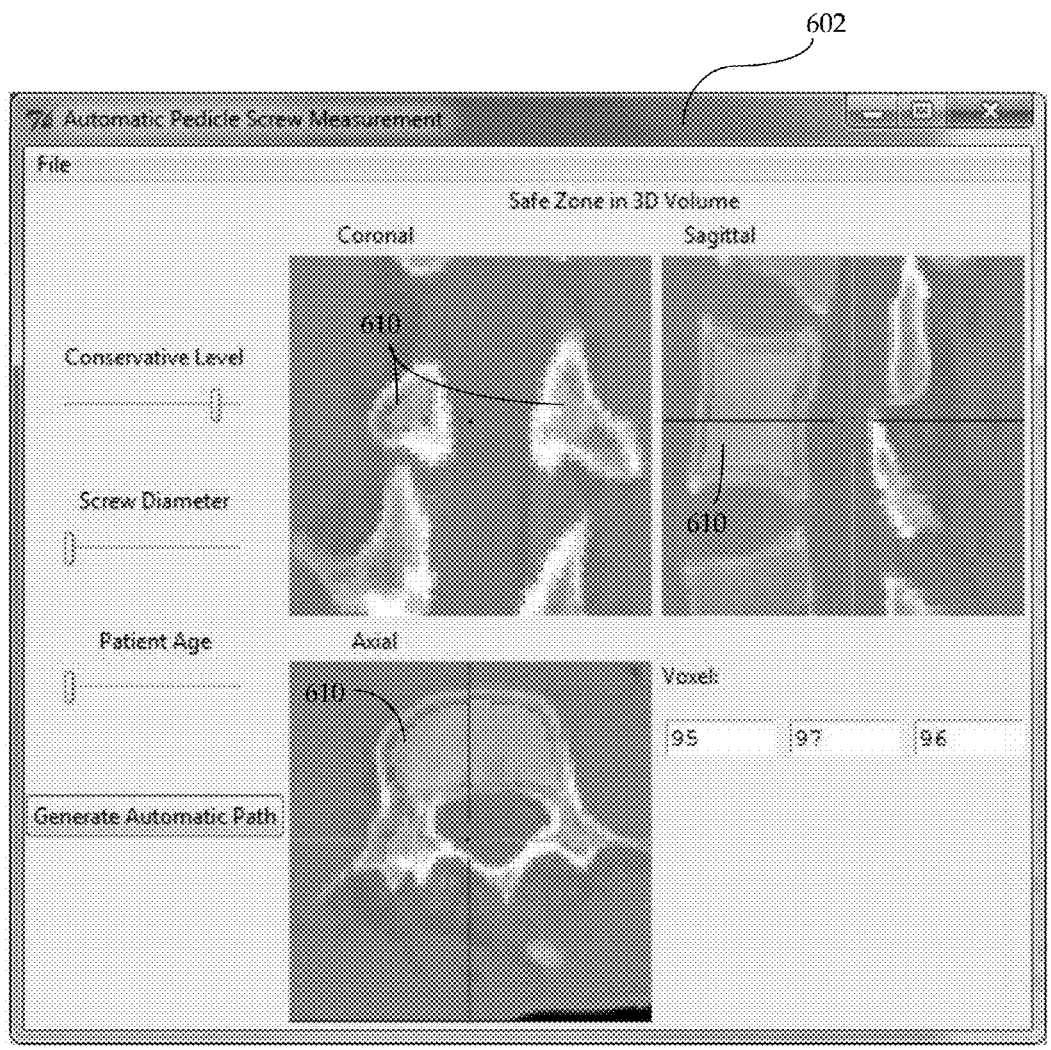
FIG. 6 shows an exemplary user interface screen indicating safe regions 610 highlighted with respect to a high conservative level.

FIG. 4 shows an exemplary user interface screen 402 indicating safe regions 410 highlighted with respect to a low conservative level. As shown, the user interface 402 is configured to provide sliding bars 404, 406 and 408 to enable the user to set the conservative level, pedicle screw diameter and patient's age. Safe regions 410 are then calculated based on these clinical parameters. Safe regions 410 are displayed in coronal, sagittal and axial views of the vertebra of interest. Safe regions 410 may be recalculated and displayed in response to any change in the clinical parameters. FIG. 5 shows an exemplary user interface screen 502 indicating safe regions 510 highlighted with respect to a mid-conservative level. FIG. 6 shows an exemplary user interface screen 602 indicating safe regions 610 highlighted with respect to a high conservative level. It can be observed that higher conservative levels result in smaller safe regions 610.

Returning to FIG. 3a, at 310, guidance generator 206 generates an optimal insertion path within the one or more safe regions that passes through the pedicle regions. Guidance generator 206 may automatically generate the optimal insertion path by performing an optimization algorithm given multiple clinical parameters (e.g., screw diameter, screw length, patient's age) while satisfying one or more pre-defined constraints. For example, the constraints may specify that the insertion path must pass through a pedicle center and be within the safe region. An exemplary optimization algorithm that may be used to determine the optimal insertion path includes the grid search optimization algorithm.

As shown in FIG. 3b, optimal insertion paths 342a-b for pedicle screws 338a-b may be generated within the safety zone. The optimal insertion paths 342a-b pass through the respective pedicle centers 336a-b. A joint optimization algorithm may be performed to generate the two optimized insertion paths 342a-b given one or more clinical parameters and satisfying one or more pre-defined constraints. For example, the constraints may specify that the insertion paths pass through respective centers of the pedicle regions and be within the safe region. The joint optimization algorithm may satisfy a further pre-defined constraint that specifies that the two optimal insertion paths 342a-b intersect. Alternatively, the pre-defined constraint may specify that the optimal insertion paths 342a-b do not intersect. The pedicle screws 338a-b may be inserted as deep into the vertebral body 334 as possible without breaking through the wall of the vertebral body 334.

Figure 7:
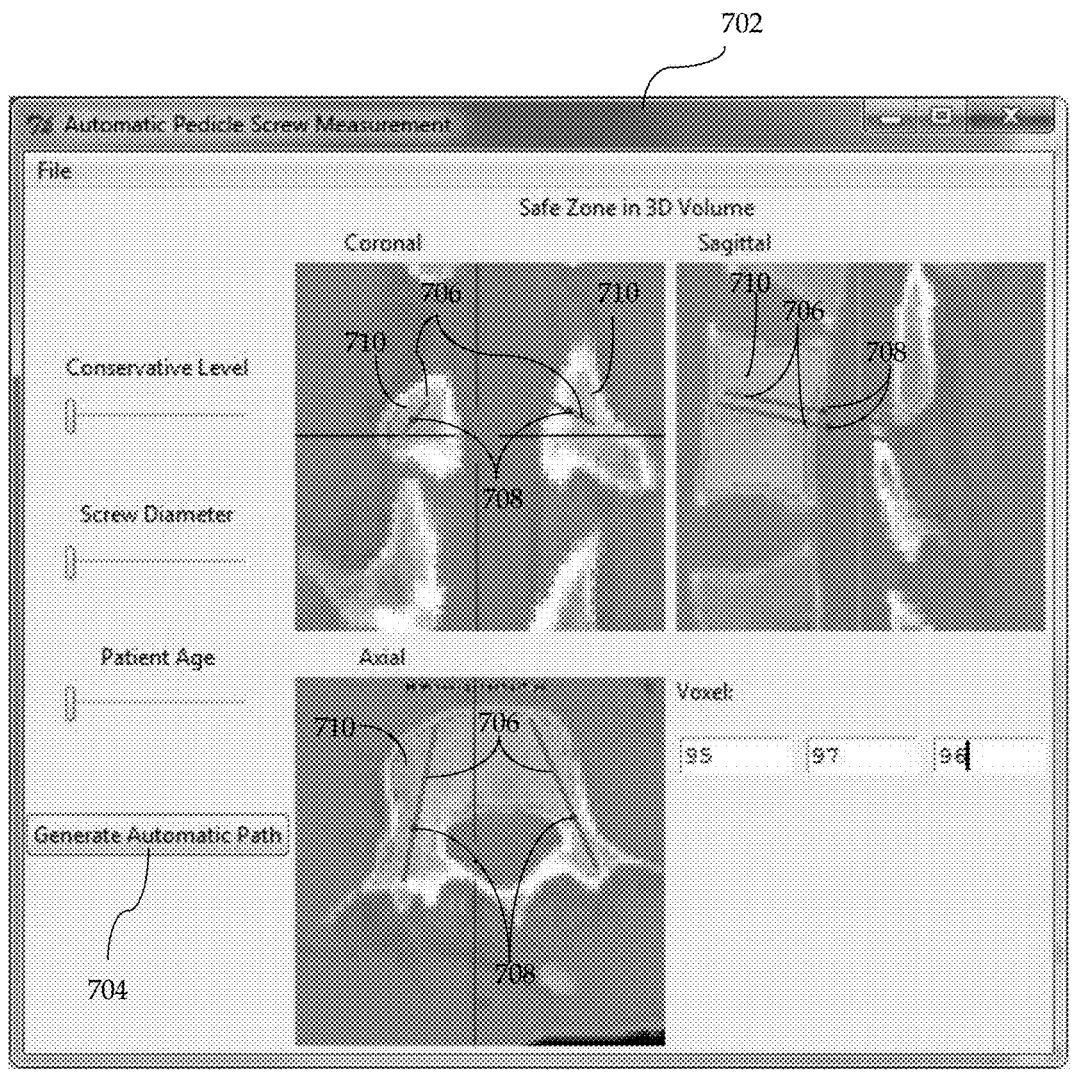
FIG. 7 shows an exemplary user interface screen displaying a pedicle screw insertion path.

At 312, guidance generator 206 generates one or more images showing the optimal insertion path. The image may be displayed at, for example, workstation 203. FIG. 7 shows an exemplary user interface screen 702 displaying a pedicle screw insertion path 706. In response to a user selecting the button 704, guidance generator 206 generates the pedicle screw insertion path 706 superimposed on the coronal, sagittal and axial view images of the vertebra of interest. As shown in the images, each insertion path 706 passes through the pedicle center 708 and is located completely within the safe region 710. Such images may be used to accurately and efficiently guide the placement of pedicle screws during a spine surgery. Derived parameters, such as maximum width and minimum length of the pedicle screw, may also be displayed as recommendations for design of the treatment plans.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. One or more non-transitory computer readable media embodying a program of instructions executable by machine to perform operations for pedicle screw positioning, the operations comprising:
    receiving image data of at least a portion of a spine;
    segmenting at least one vertebra of interest in the image data to generate segmentation results;
    generating a vertebral distance map based on the segmentation results;
    determining two pedicle regions within the segmented vertebra of interest based on the vertebral distance map;
    determining one or more safe regions within the segmented vertebra of interest by performing a thresholding algorithm based on the vertebral distance map;
    generating two optimal insertion paths within the one or more safe regions, wherein the two optimal insertion paths pass through respective centers of the pedicle regions; and
    displaying the two optimal insertion paths for pedicle screw positioning.

2. The one or more non-transitory computer readable media of claim 1 wherein the two optimal insertion paths are generated by performing a joint optimization algorithm given one or more clinical parameters while satisfying one or more pre-defined constraints.

3. The one or more non-transitory computer readable media of claim 2 wherein the one or more clinical parameters comprise a patient's age, a diameter or length of the pedicle screw, or a combination thereof.

4. The one or more non-transitory computer readable media of claim 2 wherein the one or more pre-defined constraints specify that the optimal insertion paths pass through the respective centers of the pedicle regions and are within the one or more safe regions.

5. A system comprising:
    a non-transitory memory device for storing computer readable program code; and
    a processor in communication with the memory device, the processor being operative with the computer readable program code to perform operations including
        segmenting at least one vertebra of interest in image data to generate segmentation results,
        generating a vertebral distance map based on the segmentation results,
        determining a pedicle region within the segmented vertebra of interest based on the vertebral distance map,
        determining a safe region within the segmented vertebra of interest by performing a thresholding algorithm based on the vertebral distance map,
        generating an optimal insertion path within the safe region, wherein the optimal insertion path passes through the pedicle region, and
        displaying the optimal insertion path for pedicle screw positioning.

6. The system of claim 5 wherein the processor is operative with the computer readable program code to segment the vertebra of interest by using a trained machine learning-based engine to detect landmarks of the vertebra of interest in the image data.

7. The system of claim 5 wherein the processor is operative with the computer readable program code to segment the vertebra of interest by performing a multi-atlas segmentation scheme including registering vertebral atlases to target vertebrae and deriving the segmentation results based on the registered vertebral atlases.

8. The system of claim 5 wherein the processor is operative with the computer readable program code to determine the pedicle region by performing clustering and morphological operations based on the vertebral distance map.

9. The system of claim 5 wherein the processor is operative with the computer readable program code to adaptively determine the safe region based on one or more clinical parameters including age of a patient.

10. The system of claim 5 wherein the processor is operative with the computer readable program code to determine the safe region by
    determining a distance of each voxel within the segmented vertebra of interest from a nearest vertebral edge, and
    in response to the distance being greater than a threshold distance, assigning the voxel to the safe region.

11. The system of claim 10 wherein the threshold distance is associated with a conservative value.

12. The system of claim 11 wherein the processor is operative with the computer readable program code to generate a user interface configured to enable a user to input the conservative value.

13. The system of claim 5 wherein the processor is operative with the computer readable program code to automatically derive a maximum diameter of the pedicle screw based on the safe region.

14. The system of claim 5 wherein the processor is operative with the computer readable program code to automatically derive a minimum length of the pedicle screw based on the safe region.

15. The system of claim 5 wherein the processor is operative with the computer readable program code to generate the optimal insertion path by performing an optimization algorithm given one or more clinical parameters and satisfying one or more pre-defined constraints.

16. The system of claim 15 wherein the one or more clinical parameters comprise a patient's age, a diameter or length of the pedicle screw, or a combination thereof.

17. The system of claim 16 wherein the processor is operative with the computer readable program code to generate a user interface configured to enable a user to input the one or more clinical parameters.

18. The system of claim 15 wherein the one or more pre-defined constraints specify that the optimal insertion path passes through a center of the pedicle region and is within the safe region.

19. A method comprising:
    segmenting at least one vertebra of interest in image data to generate segmentation results;
    generating a vertebral distance map based on the segmentation results;
    determining a pedicle region within the segmented vertebra of interest based on the vertebral distance map;

determining a safe region within the segmented vertebra of interest by performing a thresholding algorithm based on the vertebral distance map;

generating an optimal insertion path within the safe region, wherein the optimal insertion path passes through the pedicle region; and displaying the optimal insertion path for pedicle screw positioning.

20. The method of claim 19 wherein determining the safe region comprises adaptively determining the safe region based on one or more clinical parameters including age of a patient.

* * * * *